United States Patent
Fabian et al.

(10) Patent No.: US 6,861,527 B1
(45) Date of Patent: Mar. 1, 2005

(54) NITRATION IN A STATIC MICROMIXER

(75) Inventors: Kai Fabian, Wilhelmsfeld (DE); Joeran Stoldt, Weiterstadt (DE); Hanns Wurziger, Darmstadt (DE); Norbert Schwesinger, Eching (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/048,157

(22) PCT Filed: Jul. 5, 2000

(86) PCT No.: PCT/EP00/06317

§ 371 (c)(1),
(2), (4) Date: Sep. 3, 2002

(87) PCT Pub. No.: WO01/09065

PCT Pub. Date: Feb. 8, 2001

(30) Foreign Application Priority Data

Jul. 29, 1999 (DE) ......................................... 199 35 692

(51) Int. Cl.$^7$ ...................... C07D 217/02; C07D 201/08
(52) U.S. Cl. ........................ 546/139; 564/411; 549/462
(58) Field of Search ................................ 546/139, 109; 549/462; 564/411

(56) References Cited

FOREIGN PATENT DOCUMENTS

WO     99 22858     5/1999

*Primary Examiner*—Zinna Northington Davis
(74) *Attorney, Agent, or Firm*—White Zelano & Branigan, P.C.

(57) ABSTRACT

The present invention relates to a novel process for the nitration of organic compounds, preferably of aromatic and heteroaromatic compounds, using nitrating reagents which are known from the literature and new types of nitrating reagents.

15 Claims, 2 Drawing Sheets

Figure 1:
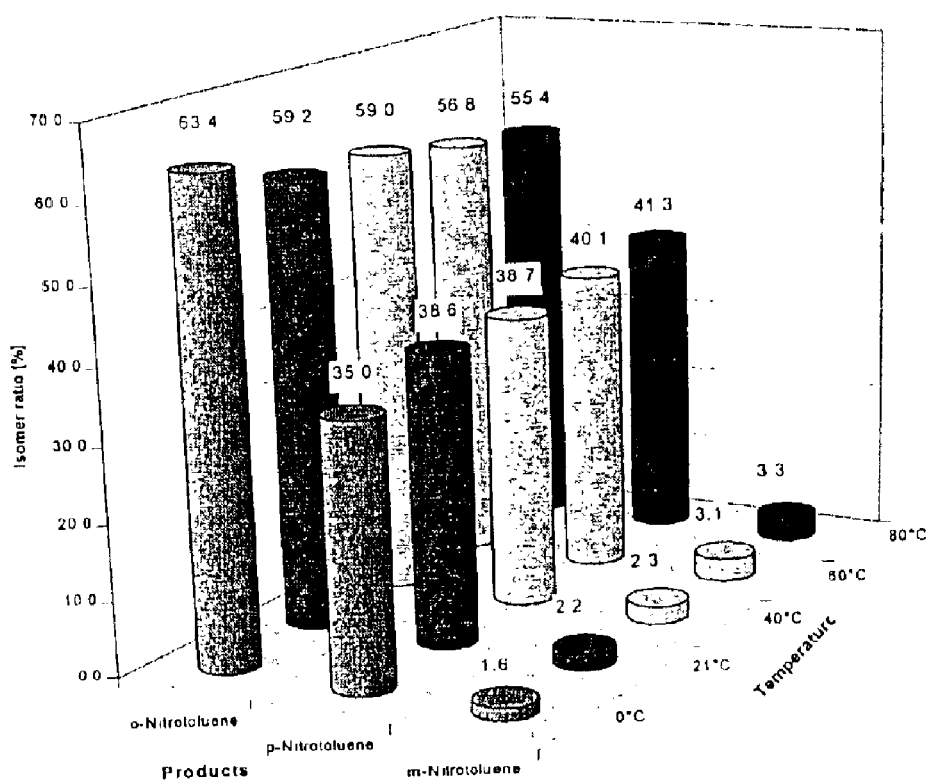

Influence of temperature on the nitration of toluene
(acetyl nitrate, 20 µl/min)

NITRATION IN A STATIC MICROMIXER

The present invention relates to a novel process for the nitration of organic compounds, preferably of aromatic and heteroaromatic compounds, using nitrating reagents which are known from the literature and new types of nitrating reagents.

The nitration of organic substrates is a very important and frequently performed process in the chemical industry. Numerous publications relate to this subject.

Particular safety problems exist on performance of nitrations on an industrial scale, since firstly in some cases highly toxic chemical substances have to be used which, even considered alone, represent a considerable risk to the environment. Secondly, nitrations generally proceed in a highly exothermic manner, which means that there is an increased risk of explosion when carrying out these reactions.

There has hitherto been no lack of attempts to reduce these safety problems. However, as soon as large amounts of nitrated products are to be prepared and a scale-up is to be carried out, the above-mentioned safety problems come to the fore.

The object of the present invention was therefore to provide a novel process which is simple to carry out and an apparatus which enable nitrations of organic compounds, in particular of aromatic and heteroaromatic compounds, to be carried out in a simple, reproducible manner with increased safety, with reduced residual risk to the environment. A further object of the invention was to provide correspondingly nitrated products in increased yields and improved purities.

The object is achieved by a process for the nitration of aromatic or heteroaromatic compounds in which the aromatic or heteroaromatic compound in liquid form or in solution is mixed intensively and allowed to react with a liquid or dissolved nitrating reagent, selected from the group consisting of dilute nitric acid, 100% nitric acid, potassium nitrate in 100% sulfuric acid, mixtures of nitric acid and sulfuric acid ("nitrating acid"), nitric acid esters, mixtures of nitric acid with inorganic and organic anhydrides and dinitrogen pentoxide, in a microreactor for an adequate residence time, and the desired nitration product is isolated from the resultant reaction mixture.

The microreactor used when carrying out the process is preferably a heatable flow reactor.

The object is furthermore achieved by a process which can be carried out continuously.

A particular variant of the process according to the invention consists in that
a) the aromatic or heteroaromatic compound is firstly derivatised,
b) the resultant derivative is dissolved in a solvent and
c) nitrated in a micromixer using a nitrating reagent, and
d) the nitrated product is isolated from the resultant solution.

The nitrated product is preferably separated off from the reaction mixture by extraction with a solvent, since this represents a simple form of work-up.

In accordance with the invention, the reaction mixture is pumped into the microreactor in such a way that it flows through the latter at a flow rate of at least 5 $\mu$l/min, and the reaction is carried out at a temperature in the range from −10 to 80°. At the same time, the course of the reaction is, if desired, monitored by gas chromatography. If desired, this can be carried out continuously.

If desired, the process according to the invention is carried out after the aromatic or heteroaromatic compound has been converted into a carbamate in a first reaction step.

In particular, the process according to the invention is used for the nitration of compounds selected from the group consisting of toluene, 1,2,3,4-tetrahydro-isoquinoline, N-methoxycarbonyl-1,2,3,4-tetrahydroisoquinoline and benzo-furan derivatives.

Various publications and patent applications disclose miniaturised flow reactors for organic reactions. Reactors of this type are preferably produced from thin silicon structures bonded to one another. Miniaturised reactors of this type have very narrow channels which, per se, tend to block very easily due to particles present or formed in the reaction solution.

The prerequisites for the ability to carry out a reaction in miniaturised flow reactors of this type therefore consist in that it can be carried out in the homogeneous liquid phase, and precipitations or the formation of particles during the reaction can be prevented.

In order to achieve the present object, numerous attempts to nitrate organic compounds, in particular aromatic and heteroaromatic compounds, have been carried out.

8-Nitro-N-methoxycarbonyltetrahydroisoquinoline, for example, is required as intermediate for the synthesis of chemical compounds used as active ingredients for the preparation of medicaments. This compound can be prepared by methods known from the literature, to be precise by nitration of 1,2,3,4-tetrahydroisoquinoline using potassium nitrate in concentrated sulfuric acid followed by acylation in accordance with the general reaction equation given below:

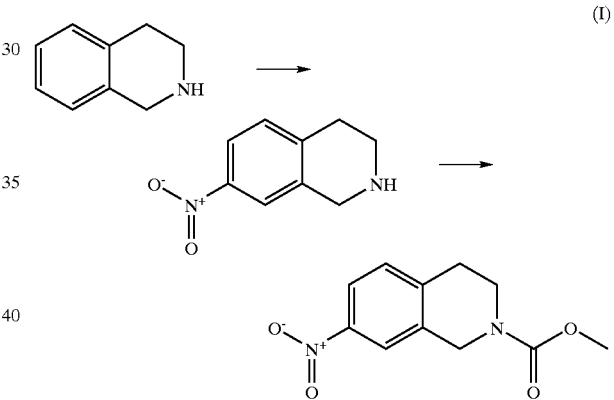

(I)

As part of the experimental programme mentioned above, it has been attempted to carry out this reaction with the aid of a microreactor. However, owing to the viscosity of 100% sulfuric acid, a considerable pressure built up in the micromixer and in the thin Teflon tubes. It has been found that this problem can be overcome with the aid of an injection pump operating at very low pump output.

Subsequent experiments showed very efficient nitration results. When the reaction was complete, a liquid reaction mixture was obtained which had to be neutralised before the desired products were separated off.

However, since the aim was to provide a process which can be carried out simply and in an environmentally friendly manner, alternatives were sought.

Surprisingly, it has been found that an altered sequence of the synthesis enables this problem to be circumvented.

In a first step, 1,2,3,4-tetrahydroisoquinoline is converted into the corresponding carbamate. The carbamate is dissolved in a suitable solvent, such as, for example, dichloromethane, and nitrated at ambient temperature using 65% nitric acid.

Optimisation experiments have shown that this nitration can be carried out at a flow rate of 5 $\mu$l/min in the microreactor with a good result, based on the ratio of starting compounds employed to product obtained. The nitration product obtained in this way can advantageously be isolated directly from the acidic reaction solution by extraction.

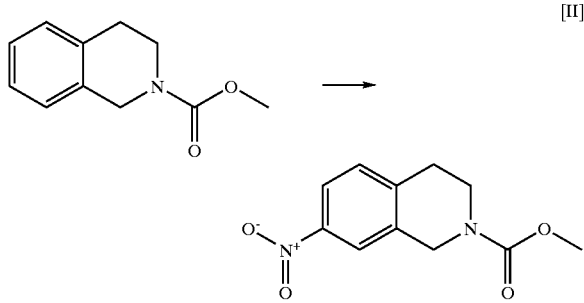

The process thus found for carrying out the desired reaction in a microreactor through which flow takes place is superior to a reaction in the stirred reactor usually used.

A very particular advantage is that, as soon as the performance parameters, such as temperature and flow rate, have been set and the system is in equilibrium, the reaction can be carried out continuously as long as there is a need for the desired reaction product. In addition, the product can be obtained in constant quality with stable yields. Correspondingly impressive results have been achieved, for example, in the nitration of N-methoxy-carbonyl-1,2,3,4-tetrahydroisoquinoline in a continuous reaction, with the latter being maintained at equilibrium for the duration of six days.

The possibility of using the microreactor for further aromatic and heteroaromatic compounds-has also been investigated. The nitration of toluene is described here in greater detail by way of example.

In a first series of experiments, toluene was mixed with an equivalent amount of dichloromethane and nitrated at various temperatures using 65% nitric acid. The ratio of the nitrated isomers to unreacted toluene is shown in the following table. The data are based on reactions at 10, 20 and 30° C. The isomer ratio was determined from HPLC analyses. However, the HPLC signals were not separated from one another sufficiently cleanly to allow the amount of meta-isomers formed to be determined precisely. However, it can be concluded from the results obtained that the results achieved correspond to those from the literature.

| Temperature [° C.] | Ortho-nitrotoluene | Para-nitrotoluene | Toluene |
|---|---|---|---|
| 0 | 41% | 22% | 37% |
| 20 | 59% | 40% | — |
| 30 | 59% | 41% | — |
| Literature[2] | 59% | 37% | |

For comparison, toluene in undiluted form was nitrated at various temperatures using 100% nitric acid. The results are shown in FIG. 1. It can be seen therefrom that the proportion of the ortho-product drops with increasing temperature, while the formation of the para-substituted toluene and the meta-form formed in small amounts increases.

Figure 2:
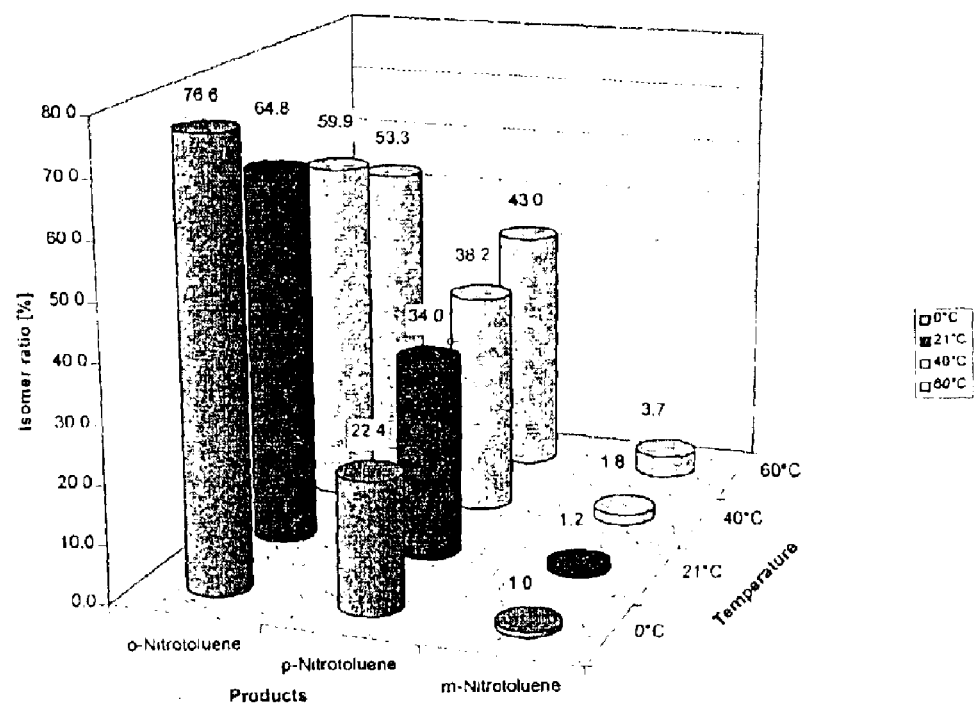

Provided that, during passage through the microsystems, all substances remain in the dissolved liquid phase and do not precipitate out, all nitrations can be carried out using the following nitrating reagents described in the literature:

dilute nitric acid
100% nitric acid
potassium nitrate in 100% sulfuric acid
mixtures of nitric acid and sulfuric acid ("nitrating acid")
nitric acid esters, in general
mixtures of nitric acid with inorganic and organic anhydrides
dinitrogen pentoxide The nitrations described proceed with good to very good yields in the static micromixer. The selectivity can be influenced by varying various parameters, such as, for example, concentration, temperature (see FIG. 2) or residence time.

The advantage of nitration in microfluid systems consists in better mass and heat transport, improved control of the reaction time and increased safety. The very small amounts of reagent present in the system are responsible for this.

This point is particularly important in the case of nitrations, which are generally highly exothermic, if, for example, the mixture consisting of 100% nitric acid and acetic anhydride, which reacts very selectively—the reactive species is the acetyl nitrate, which decomposes in an explosive manner at about 60° C.—is employed.

A change in the residence time by variation of the pump output exhibited only a slight effect on the selectivity, or none at all, in this case. It can also be assumed that the activity of the nitrating reagents and the temperature have virtually no effect on the quantitative result of the reaction at a defined residence time.

This effect is significantly more pronounced if a mixture of toluene and acetic acid is treated with 100% nitric acid. In this case, the reacting reagent is acetyl nitrate, which is in some cases, depending on the species to be nitrated, regarded as a significantly more reactive, but also more selective nitrating reagent than nitric acid alone.

A mixture consisting of nitric acid and acetic anhydride or pre-distilled acetyl nitrate is a strong, but also hazardous reagent since it decomposes above 60° C.

By means of this-reagent, it is even possible to nitrate heterocyclic compounds, which otherwise can only be nitrated with difficulty. For understandable reasons, however, this method normally only finds limited use.

In contrast to the situation in the industrial plants usually used for carrying out chemical reactions, firstly the temperature of the reaction mixture can be kept constant in each volume element in the micromixer systems according to the invention in accordance with the process according to the invention. Secondly, only very small amounts of starting material are present in the apparatus at any point in time. This means that the nitration reactions described, which were hitherto only possible using special and expensive safety precautions, can be carried out readily in the present micromixer system.

The process according to the invention can be used in a simple manner for carrying out, for example, nitrations of toluene, 1,2,3,4-tetrahydroisoquinoline, N-methoxycarbonyl-1,2,3,4-tetrahydroisoquinoline and of benzofuran derivatives.

Suitable aromatic compounds are furthermore all monocyclic and polycyclic, homoaromatic or heteroaromatic compounds, as well as compounds which have a monocyclic or polycyclic, homoaromatic or heteroaromatic basic structure or partial structure, for example in the form of substituents.

Suitable aromatic compounds are, in particular:
benzene and derivatives thereof,
naphthalene and derivatives thereof, azulene and derivatives thereof,
anthracene and derivatives thereof,
phenanthrene and derivatives thereof,
pyrene and derivatives thereof,
fluorene and derivatives thereof,
quinones, such as, for example, ortho- and para-benzoquinone, and
derivatives thereof, all naphthoquinones known to the person skilled in the art and derivatives thereof, fluorenones, anthrones, phenanthrones, all known anthraquinones and derivatives thereof.

Heteroaromatic compounds which can be employed, are the following:
oxygen-containing heteroaromatic systems (furans), such as, for example,
benzo-fused furans and derivatives thereof,
dibenzofurans and derivatives thereof,
dibenzodioxanes and derivatives thereof,
pyrylium cations and derivatives thereof,
benzopyranones and derivatives thereof,
nitrogen-containing heteroaromatic systems and derivatives thereof, such as, for example,
pyrroles, pyrazoles, imidazoles, triazoles, tetrazoles, pyridines, pyrazines,
pyrimidines, pyridinium salts, triazines, tetrazines, pyridine-N-oxide and derivatives thereof
benzo-fused pyrroles (indoles, carbazoles, benzimidazoles and benzotriazoles) and derivatives thereof,
phenazine and derivatives thereof,
quinolines and isoquinolines,
chinnolines, quinazolines and quinoxalines,
phenanthrolines and derivatives thereof,
bipyridyls and higher homologues,
acridines, acridones and derivatives thereof,
pyrene and derivatives thereof,
suitable sulfur-containing heteroaromatic systems and derivatives thereof are, for example,
thiophenes and derivatives thereof,
benzo-fused thiophenes (benzothiophenes and dibenzothiophenes) and derivatives thereof.

It is also possible to employ acenaphthylene, thiazoles, isothiazoles, biphenylenes, purines, benzothiadiazoles, oxazoles and isooxazoles in the process according to the invention.

Suitable solvents for these nitrations are the following:
dilute and concentrated acids, such as, for example, sulfuric acid, nitric acid, acetic acid and trifluoroacetic acid
acid anhydrides, such as, for example, acetic anhydride and trifluoroacetic anhydride
mixtures of acids and salts, such as, for example, concentrated sulfuric acid and $KNO_3$, and also any other combination
halogenated hydrocarbons, such as, for example, chloroform, carbon tetrachloride, dichloromethane and tetrachloroethane
esters, such as, for example, ethyl acetate
ethers, such as, for example, tetrahydrofuran, diethyl ether and tert-butyl methyl ether
mixtures of the said solvents of all types
ionic solvents, such as, for example, 1-ethyl-3-methylimidazolium tetrachloroaluminate, n-butylpyridinium tetrachloroaluminate or 1-ethyl-3-methylimidazolium tetrafluoroborate.

Suitable solvents for the work-up/extraction are all organic solvents, in particular:
ethers, such as, for example, diethyl ether, tert-butyl methyl ether, tetrahydrofuran, etc.
halogenated hydrocarbons, such as, for example, chloroform, carbon tetrachloride, dichloromethane, tetrachloromethane and tetrachloroethene
alcohols, such as, for example, methanol, ethanol, 1- and 2-propanol
nitriles, such as, for example, acetonitrile
ketones, such as, for example, acetone
esters, such as, for example, ethyl acetate.

Suitable for carrying out the nitrations described are micromixers as described, for example, in WO 96/30113 A1. Also suitable, however, are static micromixers of simpler design which effect sufficiently intensive mixing of the liquids employed in simple crossing channels and in which an adequate residence time of the reaction mixture for the reaction in the reactor is ensured.

Basic prerequisites for the suitability of microreactors in the nitration process according to the invention are furthermore:
the possibility of uniform temperatures in each volume element of the reactor,
leak-proof and reliable connection means for supply and discharge lines for liquids, but where appropriate also for further equipment for reaction monitoring or for analytical purposes,
leak-proof connection of the individual parts or structures forming the microreactor, both internally and to the outside, so that the liquid-carrying channels are separate from one another and the liquid cannot escape to the outside,
easy handling in the event of faults.

For better understanding and in order to illustrate the present invention, examples are given below which are within the scope of protection of the present invention, but are not suitable for restricting the invention to these examples. The term "within the scope of the present invention" is also taken to mean, as already stated above, nitrations carried out using static miniaturised flow reactors which are likewise known to the person skilled in the art, but where the flow reactors used can allow larger flow rates for the preparation of larger amounts of product in the same time unit, and further both uniform temperatures and homogeneous mixing are ensured in each volume element of the reactor.

EXAMPLES

Example 1

1 g of 1,2,3,4-tetrahydroisoquinoline was carefully dissolved in 5 ml of concentrated sulfuric acid. The nitric acid was prepared by dissolving 1 g of potassium nitrate in 5 ml of concentrated sulfuric acid. Two 2 ml disposable plastic syringes were filled with the two solutions and attached to a Harvard Apparatus pump 22. The disposable syringes themselves were connected to a static silicon mixer, which was in turn connected to a thin Teflon tube having a diameter of 0.25 mm and a length of 80 cm. The reaction was carried out at ambient temperature at a flow rate of 5 µl/min. The reaction mixture formed was collected in a vessel filled with ice pieces and neutralised using 2N NaOH before the product formed was extracted with dichloromethane.

1 g of 1,2,3,4-tetrahydroisoquinoline, dissolved in 5 ml of dichloromethane, was nitrated as described above at ambient temperature using 65% nitric acid and a flow rate of 5

μl/min. The work-up of the organic phase was carried out without prior neutralisation.

The same conditions were set for a continuous experiment, which was carried out continuously over six days. In this case, two syringes each with a capacity of 50 ml were used.

Example 2

A disposable plastic syringe having a capacity of 2 ml was filled with a 1:1 mixture consisting of toluene and dichloromethane. A second syringe was filled with 65% nitric acid. These two syringes were connected, and a flow rate of 5 μl/min was set. Under these conditions, the reaction was carried out at 0, 20 and 30° C.

The course of the reaction was monitored and recorded using a Merck Hitachi HPLC instrument (L 6200 pump, variable wavelength UV detector and D 2500 chromato integrator). The separating column used was a Merck Lichrocart® RP Select B 250/4.
Solvent:
Mixture of 70% of acetonitrile and 30% of water, mixed with 1% of trifluoroacetic acid
Flow rate: 0.6 ml/min
Detector wavelength: 215 nm.

The nitrations of toluene were monitored with the aid of a Hewlett-Packard 6890 series GC system with an HP 5973 mass selection detector.

In order to carry out the experiments with 100% nitric acid, one syringe was filled with nitric acid and the other with pure toluene. The nitrations were carried out at 0, 21, 40, 60 and 80° C.

In order to carry out the experiments with acetyl nitrate, one syringe was filled with a 1:1 mixture consisting of toluene and acetic anhydride and another was filled with 100% nitric acid. The contents of the two syringes were pumped simultaneously into two different inlet channels of a micromixer for intensive mixing and nitration. The nitrations were carried out at −10, 0, 21, 40 and 60° C., with the course of the reaction being monitored as described above.

What is claimed is:

1. A process for the nitration of an aromatic or a heteroaromatic compound, comprising mixing the aromatic or heteroaromatic compound in liquid form or in solution intensively and reacting in a homogeneous phase with a liquid or dissolved reagent in a microreactor for an adequate residence times, wherein intensive mixing is achieved by crossing channels within said microreactor wherein said liquid or dissolved reagent is dilute nitric acid, 100% nitric acid, potassium nitrate in 100% sulfuric acid, a mixture of a nitric acid and a sulfuric acid, a nitric acid ester, a mixture of a nitric acid with an inorganic or an organic anhydride, or a dinitrogen pentoxide, and
isolating a desired nitration product from a resultant reaction mixture.

2. A process according to claim 1, wherein the microreactor used is a heatable flow reactor.

3. A process according to claim 1, wherein the process is continuous.

4. A process according to claim 1, comprising:
a) first derivatizing the aromatic or heteroaromatic compound,
b) dissolving the resultant derivative in a solvent and
c) nitrating in a micromixer using a nitrating reagent.

5. A process according to claim 1, wherein the nitrated product is separated off from the reaction mixture by extraction with a solvent.

6. A process according to claim 1, further comprising flowing the reaction mixture through the microreactor at an adequate flow rate of from 1 μl/min=10 ml/min, carrying out the reaction at a temperature in the range of −40=150° C., and monitoring the reaction by gas chromatography.

7. A process according to claim 6, wherein the reaction mixture flows through the microreactor at a flow rate of 5 μl/min=1 ml/min, the reaction temperature is −10=80° C., and the reaction is monitored, optionally continuously, by gas chromatography.

8. A process according to claim 4, wherein an aromatic or a heteroaromatic compound is converted into a carbamate in a first reaction step.

9. A process according to claim 1 for the nitration of an aromatic or a heteroaromatic of toluene, 1,2,3,4-tetrahydroisoquinoline, N-methoxycarbonyl-1,2,3,4-tetrahydroisoquinoline or a benzofuran compound or a compound derived therefrom.

10. A process according to claim 1, wherein the nitration product is 8-nitro-N-methoxycarbonyl-tetrahydroisochinolin.

11. A process for nitrating an aromatic or a heteroaromatic compound comprising reacting the aromatic or heteroaromatic compound with a reagent comprising a nitric acid, a potassium nitrate in a sulfuric acid, a mixture comprising a nitric acid and a sulfuric acid, a nitric acid ester, a mixture comprising a nitric acid and an inorganic or an organic anhydride, or a dinitrogen pentoxide in a homogeneous phase in a microreactor.

12. A process according to claim 11, further comprising isolating a desired nitration product from a resultant reaction mixture.

13. A process according to claim 11, wherein the aromatic compound is a benzene, a naphthalene, an azulene, an anthracene, a phenanthrene, a pyrene, a fluorene, a quinone, a naphthoquinone, a fluorenone, an anthrone, a phenanthrone, an anthraquinone, or a compound derived therefrom.

14. A process according to claim 11, wherein the heteroaromatic compound is a benzo-fused furan, a dibenzofuran, a dibenzodioxane, a pyrylium cation, a benzopyranone, a pyrrole, a pyrazole, an imidazole, a triazole, a tetrazole, a pyridine, a pyrazine, a pyrimidine, a pyridinium salt, a triazine, a tetrazine, a pyridine-N-oxide, a benzo-fused pyrrole, a phenazine, a quinoline, an isoquinoline, a chinnoline, a quinazoline, a quinoxaline, a phenanthroline, a bipyridyl, an acridine, an acridone, a pyrene, a thiophene, a benzo-fused thiophene, an acenaphthylene, a thiazole, an isothiazole, a biphenylene, a purine, a benzothiadiazole, an oxazole, an isooxazole or a compound derived therefrom.

15. A process according to claim 11, further comprising a solvent, wherein the solvent comprises an acetic acid, a trifluoroacetic acid, a sulphuric acid, a nitric acid, an acid anhydride, a mixture of an acid and a salt, a halogenated hydrocarbon, an ester, an ether, an ionic solvent, or a mixture thereof.

* * * * *

UNITED STATES PATENT AND TRADEMARK OFFICE
CERTIFICATE OF CORRECTION

PATENT NO. : 6,861,527 B1 Page 1 of 1
APPLICATION NO. : 10/048157
DATED : March 1, 2005
INVENTOR(S) : Kai Fabian et al.

It is certified that error appears in the above-identified patent and that said Letters Patent is hereby corrected as shown below:

Column 8, line 6 reads "1µl/min=10ml/min," should read -- 1µl/min-10ml/min --
Column 8, line 7 reads "-40=150°C.," should read -- -40-150° C., --
Column 8, line 11 reads "µl/min=1ml/min," should read -- µl/min-1ml/min --
Column 8, line 11 reads "-10=80° C.," should read -- -10-80° C., --

Signed and Sealed this

Fifteenth Day of August, 2006

JON W. DUDAS
*Director of the United States Patent and Trademark Office*